(12) United States Patent
Lim et al.

(10) Patent No.: US 8,617,621 B2
(45) Date of Patent: Dec. 31, 2013

(54) **COMPOSITION FOR ENHANCING IMMUNITY CONTAINING PLANT STEM CELL LINE DERIVED FROM CAMBIUM OF *PANAX GINSENG* INCLUDING WILD GINSENG OR GINSENG AS AN ACTIVE INGREDIENT**

(75) Inventors: Min Jung Lim, Jeonbuk (KR); Young Woo Jin, Jeonbuk (KR); Eun Kyong Lee, Jeonbuk (KR)

(73) Assignees: Unhwa Corporation, Jeonju-Si, Jeollabuk-Do (KR); Young Woo Jin, Iksan-Si, Jeollabuk-Do (KR); Eun Kyoung Lee, Jeonju-Si, Jeollabuk-Do (KR)

( * ) Notice: Subject to any disclaimer, the term of this patent is extended or adjusted under 35 U.S.C. 154(b) by 0 days.

(21) Appl. No.: 13/202,868

(22) PCT Filed: Feb. 23, 2010

(86) PCT No.: PCT/KR2010/001116
§ 371 (c)(1),
(2), (4) Date: Oct. 28, 2011

(87) PCT Pub. No.: WO2010/095911
PCT Pub. Date: Aug. 26, 2010

(65) Prior Publication Data
US 2012/0039918 A1    Feb. 16, 2012

(30) Foreign Application Priority Data
Feb. 23, 2009  (KR) .................. 10-2009-0015040

(51) Int. Cl.
*A61K 36/00* (2006.01)
*A61K 36/25* (2006.01)
*A61K 39/00* (2006.01)
*A61K 45/00* (2006.01)
*C12N 5/00* (2006.01)

(52) U.S. Cl.
USPC ..... 424/728; 424/725; 424/184.1; 424/278.1; 435/410

(58) Field of Classification Search
None
See application file for complete search history.

(56) References Cited

U.S. PATENT DOCUMENTS

| | | | |
|---|---|---|---|
| 4,795,742 A * | 1/1989 | Liu | ................................. 514/26 |
| 6,432,454 B1 | 8/2002 | Shan et al. | |
| 6,555,527 B1 | 4/2003 | Yun et al. | |
| 7,067,160 B2 | 6/2006 | Shan et al. | |
| 7,186,423 B2 | 3/2007 | Shan et al. | |
| 7,413,756 B2 | 8/2008 | Shan et al. | |
| 2004/0101503 A1 * | 5/2004 | Mahe et al. | ................. 424/70.14 |

FOREIGN PATENT DOCUMENTS

| KR | 100506950 B1 | 8/2005 |
|---|---|---|
| KR | 100533120 B1 | 12/2005 |
| KR | 100780521 B1 | 11/2007 |

OTHER PUBLICATIONS

Yoshikawa et al, Saponin production by cultures of *Panax ginseng* transformed with *Agrobacterium rhizogenes*. Plant cell reports, 1987. vol. 6, No. 6. p. 449-453.*
Kim et al, Adventitous root growth and ginsenoside accumulations in *Panax ginseng* cultures as affected by methyul jasmonate, Biotechnology Letters 26: 1619-1622, 2004.*
Wang, Huamin, et al.; "Asian and Siberian ginseng as a potential modulator of immune function: an in vitro cytokine study using mouse macrophages," Clinica Chimica Acta, 2003, pp. 123-128, vol. 327.
Larsen, Maria Waldorff, et al.; "Ginseng modulates the immune response by induction of interleukin-12 production," APMIS, 2004, pp. 369-373, vol. 112.
International Search Report, Oct. 12, 2010.

* cited by examiner

*Primary Examiner* — Qiuwen Mi
(74) *Attorney, Agent, or Firm* — Tristan A. Fuierer; Andrew D. Gerschutz; Moore & Van Allen, PLLC

(57) ABSTRACT

The present invention relates to a composition for enhancing immunity, comprising one or more of the following: a homogenous cell line, and a lysate, an extract and a culture medium thereof as an active ingredient. The homogenous cell line, the lysate, the extract and the culture thereof according to the present invention, which are derived from a natural product, minimize adverse side effects of prior immune enhancing agents and safe for the human body. Further, they effectively increase the activity of NK cells responsible for innate immunity, as well as increase the proliferation rate of lymph node cells when the cells were re-exposed to an antigen in a specific immune reaction to enhance acquired immunity, and thus are useful as an immune enhancing agent. In particular, the homogenous cell line, the lysate, the extract, and the culture thereof according to the present invention also effectively increase the number of hone marrow cells, thus are not only used as an adjuvant in an immune reaction, but also used in the prevention and treatment of anemia through hematopoiesis.

9 Claims, 12 Drawing Sheets

FIG. 11

|  | Sex/age | Disease | Combination therapy | Dose | Level (normal range) | Hb 12.0-17.0 (g/dl) | PLT 130-400 (10³/mm³) | RBC 4-6.3 (10⁶/mm³) | WBC 4.5-11 (10³/mm³) | Administration period |
|---|---|---|---|---|---|---|---|---|---|---|
| SEO** | F/29 | Breast cancer | Radiation | 3 g | Before | 10.1 | 195 | 3.04 | 3.8 | 1 month |
|  |  |  |  |  | After | 12.3 | 234 | 3.7 | 5.1 |  |
| LEE** | M/55 | Hepatitis B | None | 2 g | Before | 14.7 | 111 | 5.06 | 3.2 | 1 month |
|  |  |  |  |  | After | 16.1 | 134 | 5.33 | 4.1 |  |
| LEE** | M/47 | Gastric cancer | None | 3 g | Before | 11.6 | 161 | 3.64 | 9.47 | 1 month |
|  |  |  |  |  | After | 12.9 | 160 | 4.37 | 10 |  |
| JEON** | M/19 | Germ cell tumor | Anticancer/radiation/psychiatry | 2 g | Before | 13.5 | 100 | 3.93 | 4.14 | 3 months |
|  |  |  |  |  | After | 15.6 | 145 | 4.49 | 5.55 |  |

FIG. 12

| | Sex/age | Disease | Combination therapy | Dose | Level (normal range) | Hb 120-170 (g/dl) | PLT 130-400 (10³/mm³) | RBC 4-6.3 (10⁶/mm³) | WBC 4.5-11 (10³/mm³) | Administration period |
|---|---|---|---|---|---|---|---|---|---|---|
| LEE, OO | M/42 | Gastric cancer | None | 3 g | Before | 14.2 | 191 | 4.36 | 4.55 | 5 months |
| | | | | | After | 14.9 | 226 | 4.93 | 5.53 | |
| CHA, OO | F/44 | Liver cancer | Embolization | 3 g | Before | 9.2 | 51 | 2.44 | 1.1 | 4 months |
| | | | | | After | 11.9 | 333 | 3.26 | 2.4 | |
| WON, OO | F/60 | Breast cancer | Anticancer therapy | 3 g | Before | 9.8 | 302 | 3.16 | 2.01 | 3 months |
| | | | | | After | 12.8 | 537 | 4.12 | 5.02 | |
| CHOI, OO | M/9 | Leukemia | Anticancer therapy | 2 g | Before | 9.9 | 173 | 3.12 | 2.06 | 5 months |
| | | | | | After | 11.3 | 193 | 3.39 | 2.85 | |
| SEO, OO | F/8 | Cirrhosis | None | 3 g | Before | 10.5 | 49 | 3.92 | 1.71 | 7 months |
| | | | | | After | 11.2 | 78 | 3.49 | 2 | |
| SONG, OO | F/56 | Cirrhosis | None | 3 g | Before | 10.5 | 47 | 3.18 | 2 | 3 months |
| | | | | | After | 10.6 | 59 | 3.14 | 2.4 | |
| KIM, OO | F/30 | Aplastic anemia | Anemia drug | 2.5 g | Before | 9.9 | 8 | 2.75 | 2.2 | 1 month |
| | | | | | After | 9.9 | 50 | 2.85 | 4.1 | |

COMPOSITION FOR ENHANCING IMMUNITY CONTAINING PLANT STEM CELL LINE DERIVED FROM CAMBIUM OF *PANAX GINSENG* INCLUDING WILD GINSENG OR GINSENG AS AN ACTIVE INGREDIENT

CROSS-REFERENCE TO RELATED APPLICATIONS

This application is a national phase entry application of International Application No. PCT/KR2010/01116, filed Feb. 23, 2010, which claims priority to Korean Application No. 10-2009-0015040, filed Feb. 23, 2009.

FIELD OF THE INVENTION

The present invention relates to a composition for enhancing immunity, which contains, as an active ingredient, a *Panax ginseng* cambium-derived cell line; a lysate thereof; an extract thereof; or a culture medium thereof.

BACKGROUND OF THE INVENTION

Immunity is broadly classified into innate immunity with which a person is born and acquired immunity that is obtained in the course of daily life. The innate immunity is also called "natural immunity", which responds to antigens in a non-specific manner and without particular immunological memory. The innate immune system includes skin and mucous membranes blocking the invasion of antigens, a low pH of gastric acid, and phagocytes removing harmful foreign substances such as macrophages and polymorphonuclear leukocytes. The innate immunity actually defends a host from most of the infections. Meanwhile, the acquired immunity system is characterized by its immunological memory against a previously infected antigen, and thus, it specifically responds to and effectively eliminates the antigen, when invasion occurred again.

A decline in immune function may result in a variety of immune diseases such as asthma, seasonal or perennial rhinitis, allergic sinusitis, conjunctivitis, atopic dermatitis, urticaria, hemolysis of erythrocyte, acute glomerulonephritis, and others.

It is more important to prevent these immune diseases than to treat them, but there are many problems in employing the currently available therapeutic agents for the prevention of the diseases. Thus, there is a need to develop a method for preventing and treating the immune disorders without taking the immune-enhancing agents having possible adverse effects.

Many studies have been progressed to develop new medicaments and formulations for preventing and treating the immune disorders and, in particular, have been focused on the development of anticancer agents with low adverse effects originating from natural substances. As an example, an extract for enhancing immunity derived from Korean seaweeds was developed (see, Korean Laid-open Publication No. 10-2000-00063617). However, there is still a need of superior immune-enhancing agents derived from natural substances.

Meanwhile, the concept of immune-enhancing agent was suggested by Roman, and it has started to be known to public from the observation that the administration of any immune-enhancing substance in combination with a vaccine enhanced the effect of the vaccine compared to the administration of vaccine only. In addition, the "immune-enhancing agent" refers to a substance which elevates specific or non-specific, cellular and humoral immune responses of a host, which is recently attracting much attention due to the use of immunopotentiation in the treatment of infections or tumors.

The present inventors have endeavored to develop a new composition for enhancing immunity which can prevent and treat immune disorders and has minimized adverse side effects; and have achieved the present invention by confirming that a cell line derived from the cambium of *Panax ginseng* including wild ginseng and ginseng, and a lysate, an extract and a culture medium thereof increase the activity of NK cells, and enhance the proliferation rate of the cells of lymph nodes in an antigen-specific manner.

SUMMARY OF THE INVENTION

It is an object of the present invention to provide a natural product-derived composition for enhancing immunity having minimized adverse side effect compared to prior therapeutic agents In accordance with one aspect of the present invention, there is provided a composition for enhancing immunity, comprising one or more of the following: a cell line, and a lysate, an extract and a culture medium thereof, wherein the cell line is derived from the cambium of *Panax ginseng* and in an innately undifferentiated state.

In accordance with another aspect of the present invention, there is provided a functional food for enhancing immunity, comprising one or more of the following: the cell line, and a lysate, an extract and a culture medium thereof.

In accordance with another aspect of the present invention, there is provided a method for enhancing immunity in a mammal, comprising administering to the mammal one or more of the following: the cell line, and a lysate, an extract and a culture medium thereof.

In accordance with another aspect of the present invention, there is provided a use of one or more of the following: the cell line, and a lysate, an extract and a culture thereof, for enhancing immunity.

In accordance with another aspect of the present invention, there is provided a composition for preventing or treating anemia, comprising one or more of the following: the cell line, and a lysate, an extract and a culture medium thereof.

In accordance with another aspect of the present invention, there is provided a method for preventing or treating anemia, comprising applying one or more of the following: the cell line, and a lysate, an extract and a culture thereof.

In accordance with another aspect of the present invention, there is provided a use of one or more of the following: the cell line, and a lysate, an extract and a culture thereof, for preventing or treating anemia.

Other features and embodiments of the present invention will be apparent from the following description and the appended claims.

BRIEF DESCRIPTION OF DRAWINGS

FIGS. 11 and 12 present Tables showing the measurement results of levels of hemoglobins, platelets, erythrocytes, and leukocytes before and after the administration of the cell line derived from the cambium of *Panax ginseng* according to the present invention.

DETAILED DESCRIPTION OF THE INVENTION

Figure 1:
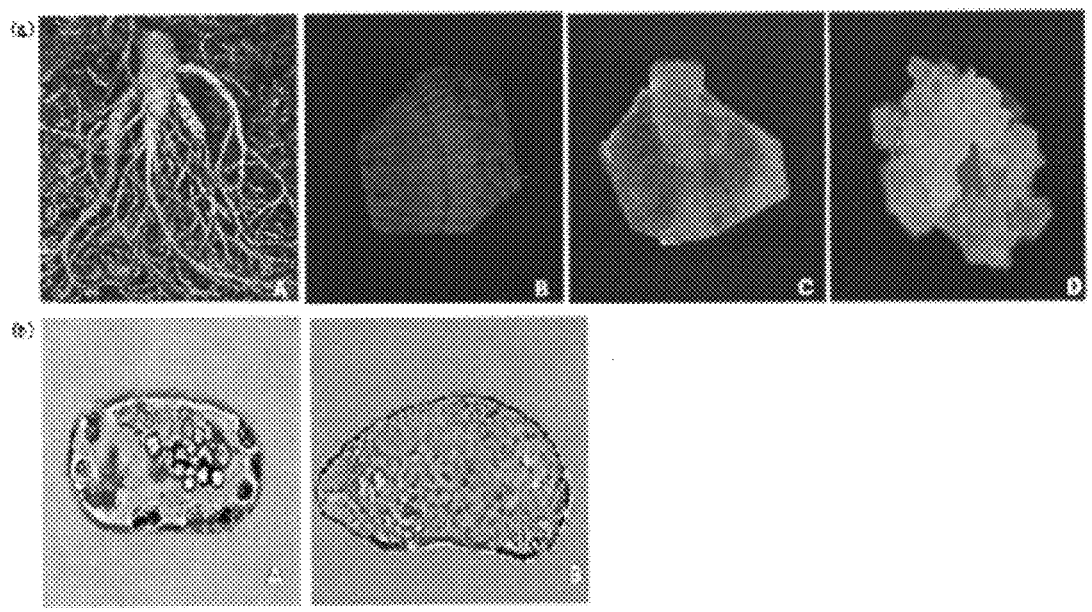
FIG. 1 displays photographs showing a process of cell line isolation according to the present invention (a), a cell line derived from the cambium of wild ginseng ((b)-A) and a callus cell line (Korea Research Institute of Bioscience and Biotechnology, KCTC PC10224) derived from the cotyledon of ginseng ((b)-B)
Figure 2:
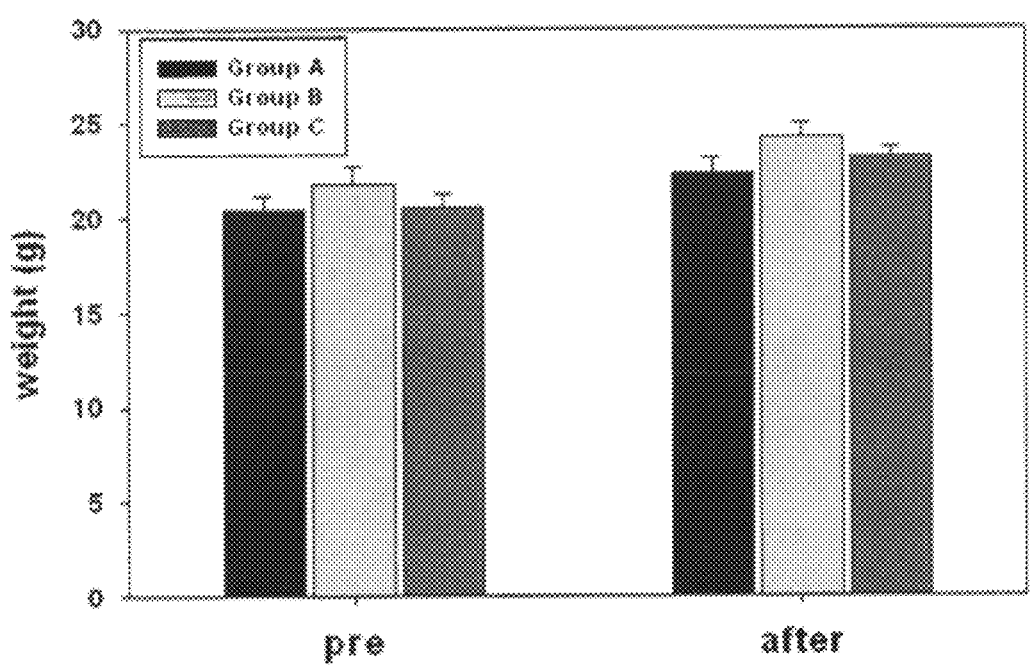
FIG. 2 presents a graph showing the body weights for a control group (A) and experimental groups (B and C) before the administration and at 14 days after the administration of the cell line according to the present invention.

Unless otherwise defined, all of technical and scientific terms used herein have the same meanings as commonly understood by one of ordinary skill in the art. Generally, the nomenclature used herein is well known in the art and commonly used.

The definitions of various terms used in the detailed description of the present invention are as follows.

The term "cambium" as used herein refers to a tissue that thickens the stem and the root to allow a plant to grow volumetrically. It was reported that when the cambium, a meristem where the cell division occurs most actively, is used as an explant for plant tissue culture, a rapid and mass production of cells is possible (Korean Patent No. 0533120).

As used herein, the term "lysate" refers to a cell lysate obtained by disrupting cells through a chemical method with, for example, a detergent, or a physical method. The term "extract" of a cell line refers to a substance obtained by dissolving cells in a solvent and isolating the cells, and the extract can be concentrated through distillation or evaporation. Herein, cell line is intended to include a cell line which goes through differentiation under culture conditions or which has improved ability to produce and/or secrete useful substances. The term "culture medium" of the cell line as used herein refers to cell culture medium in which the cell line was removed after cell culture.

The term "innately undifferentiated" as used herein refers to cells that have not become an undifferentiated state through a dedifferentiation process, but are originally maintained in a pre-differentiated state.

In one aspect, the present invention is directed to a composition for enhancing immunity, comprising one or more of the following: a cell line derived from the cambium of *Panax ginseng*, and a lysate, an extract and a culture medium thereof as an active ingredient. In the present invention, *Panax ginseng* includes wild ginseng or ginseng (Lian M. L. et al., *J. Plant Biology*, 45: 201, 2002; Han J. Y. et al., *J. Plant Biology*, 49:26, 2006; Teng W. L. et al., *Tissue and Organ Culture*, 68:233, 2002), said wild ginseng or ginseng including open field ginseng or tissue-cultured ginsengs (adventitious roots and cell lines derived therefrom).

The cell line derived from the cambium of *Panax ginseng* according to the present invention is characterized in that it is in an innately undifferentiated state. At this time, the cell line is additionally characterized in that it is present as single cell level during a suspension culture, in which "single cell level" refers that the number of single cells is more larger or it is present as cell aggregates having a smaller diameter during a suspension culture, compared to cell lines derived from a tissue other than the cambium of *Panax ginseng*, or cells induced from dedifferentiated callus tissues. Also, the cell line has further following characteristics: (a) it is morphologically characterized by multiple vacuoles; (b) it has a lower sensitivity to shear stress in a bioreactor, compared to cell lines derived from tissues other than the cambium of *Panax ginseng*; and (c) its growth rate is higher than those of cell lines derived from tissues other than the cambium of *Panax ginseng* and is cultured stably. Moreover, the cell line is characterized in that it is a homogeneous cell line.

In the present invention, the cell line may be obtained by using an isolation method comprising the steps of:

(a) obtaining a *Panax ginseng* cambium-containing storage root tissue;

(b) culturing the cambium-containing tissue in a medium supplemented with IAA (indole-3-acetic acid) or IBA (indole-3-butyric acid) to induce a cell line derived from the cambium, wherein an osmotic stress is applied to the cambium-containing tissue before, during, or after the culture; and (c) collecting the induced, cambium-derived cell line.

In step (b), the osmotic stress is used to induce a cambium-specific cell line, and is applied before the culturing to allow tissues other than cambium, i.e., cortex, phloem, xylem, or pith, to lose differentiation potential, thereby leading to necrosis when cultured with hormones specific to cambium division, e.g., IAA and IBA. At this time, preferably, an osmotic agent may be treated in a concentration of 0.5~2M, the osmotic stress may be maintained for 16 to 24 hours under refrigeration or at room temperature, and then the treated osmotic stress may be removed. However, the concentration of the osmotic agent, treatment time, and temperature may be varied depending upon a plant or tissue used and thus not limited thereto. Further, in step (b), IAA or IBA is preferably contained in an amount of 0.1~5 mg/L.

In addition, said step (c) is preferably performed by proliferating the induced cambium-derived cell line in a medium which contains one or more of 2,4-D (2,4-dichlorophenoxyacetic acid), picloram and IBA, and then collecting the cambium-derived cells. 2,4-D, picloram or IBA is preferably used in an amount of 1~5 mg/L, and, more preferably, 2 mg/L.

Further, the cell line collected in step c) may be additionally cultured in a medium supplemented with an elicitor and then collected. Examples of elicitors include raw sugar or sugar; and any substance selected from the group consisting of methyl jasmonate, an extract of fungi, an extract of bacteria, an extract of yeast, chitosan, glucomannan, glucan, phenylalanine, benzoic acid, salicylic acid, arachidonic acid, STS, mevalonate, N-benzoylglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate and sodium acetate. In addition, the elicitor may be a physical or chemical stresses such as UV, heat, light, light cycle, shear stress, ethylene, antifungal agents, antibiotics, heavy metal salts, high salt concentration, etc. Among them, methyl jasmonate or raw sugar is preferably used. Raw sugar or methyl jasmonate as elicitors is preferably added in a concentration of 3~5 wt % (g/L) of raw sugar or 50~150 µM of methyl jasmonate.

The medium used in the present invention may be any conventional medium for plant tissue culture, and examples thereof include, but are not limited to, N6 medium, SH medium, MS medium, AA medium, LS medium, B5 medium, WPM medium, LP medium, White medium, GD medium, DKW medium, DCR medium, etc.

In the present invention, the extract may be obtained by using a solvent selected from the group consisting of distilled water, lower alcohol, acetone, DMSO (dimethyl sulfoxide) and a mixture thereof. The lower alcohol refers to an alcohol having carbon numbers ranging from 1 to 5 such as methanol, ethanol, and the like.

In an embodiment of the present invention, it was confirmed that the activities of NK cells in charge of innate immunity were significantly increased by the administration of a cell line derived from the cambium of *Panax ginseng* according to the present invention. NK cells are known to play a critical role in antitumor responses and antivirus immune responses. In particular, it was shown that the activities of NK cells were more highly increased when a homogenous cell line derived from the cambium of wild ginseng was used, the cell line being obtained by additionally culturing in a medium treated with raw sugar and methyl jasmonate as elicitors. Besides, in another embodiment of the present invention, it was confirmed that a cell line derived from the cambium of *Panax ginseng* or a culture thereof according to the present invention highly increased the activities of NK cells, compared to a control group administered with adventitious roots of wild ginseng, indicating its superior immune enhancing effect.

Further, in another embodiment of the present invention, it was confirmed that the administration to a mouse of a cell line derived from the cambium of *Panax ginseng* according to the present invention immediately and rapidly increased the number of the cells of lymph node when an antigen to which the mouse had previously been exposed was introduced to the mouse again, which indicates that the cell line according to the present invention has an effect of increasing the proliferation rate of antigen-specific cells of lymph node.

Thus, it was shown that a cell line derived from the cambium of *Panax ginseng* according to the present invention is an excellent immune-enhancing agent which enhances both innate immunity and acquired immunity. While no particular Example is presented with regard to the immune-enhancing effects of a composition comprising a lysate or an extract of the inventive cell line, it would be obvious to one of skill in the art that the composition comprising a lysate or an extract of the homogenous cell line would have same or similar effects as the cell line as shown above.

The composition for enhancing immunity, comprising one or more of the cell line, and the lysate, the extract and the culture medium thereof may be provided as a pharmaceutical composition containing one or more of said cell line, and the lysate, the extract and the culture medium thereof, alone or in combination with at least one pharmaceutically acceptable carrier, excipient, or diluent. The cell line, and the lysate, the extract and the culture medium thereof may be contained in the pharmaceutical composition in a pharmaceutically effective amount, depending upon disease to be prevented or treated and its severity, the patient's age, weight, health condition and sex, the route of administration and the period of treatment.

The phrase "pharmaceutically acceptable composition" as used herein refers to a composition which is physiologically acceptable and does not cause gastric disorder, allergic responses such as vertigo, or similar responses, when administered to humans. Examples of the carrier, excipient, or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oils.

The pharmaceutical composition may further comprise fillers, anti-coagulating agents, lubricants, wetting agents, perfumes, emulsifying agents, and preservatives. In addition, the pharmaceutical composition of the present invention may be formulated using a method well known in the art, such that it can provide the rapid, sustained, or delayed release of the active ingredient after administration to mammals. The formulation may be in the form of powders, granules, tablets, emulsions, syrups, aerosols, soft or hard gelatin capsules, sterile injectable solutions, or sterile powders, etc.

Besides, the cell line derived from the cambium of *Panax ginseng*, the lysate, the extract and the culture medium thereof may be used as a food additive, and thus in another aspect of the present invention, the present invention is directed to a functional food for enhancing immunity, comprising one or more of the following: the cell line derived from the cambium of *Panax ginseng*, and the lysate, the extract and the culture medium thereof. The term 'functional food' as used herein refers to a food, the functionality of which has been enhanced by adding the homogenous cell line, or the lysate, the extract or the culture medium thereof according to the present invention.

Meanwhile, in another embodiment of the present invention, it was confirmed that the administration of the cell line and the culture thereof according to the present invention effectively increased the number of bone marrow cells. Further, it was also confirmed that the administration of the cell line and the culture medium thereof according to the present invention effectively increased the number of bone marrow cells, compared to a conventional product of wild ginseng (adventitious roots of wild ginseng). The existing radiotherapy or chemotherapy for a cancer had a problem of inevitably deteriorating immune function due to adverse side effects such as inhibiting the production of blood cells in bone marrow, while the cell line, the lysate, the extract, and the culture medium thereof increases the number of bone marrow cells, and it is thus obvious that the cell line of the present invention, and the lysate, the extract, and the culture medium thereof would be useful as an immune-enhancing agent preventing the deterioration of immune function.

In addition, such increase in bone marrow cells indicates that the cell line according to the present invention has an activity of strengthening hematopoiesis, and this action provides preventive and therapeutic effects on anemia. Thus, in another aspect of the present invention, the present invention is directed to a composition for preventing or treating anemia, comprising one or more of the following: the cell line derived from the cambium of *Panax ginseng*, and a lysate, an extract and a culture medium thereof.

EXAMPLES

Hereinafter, the present invention is described in more detail. The following Examples are given for the purpose of illustration only, and are not intended to limit the scope of the invention.

In particular, while the immune enhancing effects were confirmed using a cell line derived from the cambium of wild ginseng and a culture medium thereof in the following Examples, it would be readily appreciated by one of ordinary skill in the art that a lysate or an extract thereof would also have the same or similar effects as the cell line.

Example 1

Preparation of Homogeneous Cell Line Derived from Cambium of *Panax ginseng*

1-1: Preparation of Plant Materials (1) FIG. 1(*a*)-A shows typical appearance of wild ginseng used in the present invention. Wild ginseng was purchased, washed with running tapwater to remove soil, dirt, or other contaminants on its surface, its main root was again washed with a liquid detergent, and kept in running water. The washed root was placed into a sterilized flask in a clean bench, and then sterilized with 70% ethanol for about 30 sec to 1 min. Then, the tissue was rinsed out with sterile distilled water, and treated with an antiseptic solution containing 1% to 1.5% of sodium hypochlorite (Junsei, Japan) for 5 to 15 min. At this time, several drops of TWEEN® 20 (Polyoxyethylenesorbitan monolaurate, Junsei, Japan) were added to allow the antiseptic solution to effectively penetrate into the tissue. After the process, the main root was rinsed out with sterile distilled water 3 to 5 times. Then, in order to prevent browning, the sterilized main root was placed in BIM (browning inhibition medium) containing an antioxidant, shook for 30 min to 1 hr, and then placed onto a sterilized filter paper to remove moisture.

The composition and concentration of BIM used are shown in Table 1.

TABLE 1

Composition and concentration of BIM

| Ingredients | Concentration |
|---|---|
| McCown WPM salt | ¼ strength |
| Sucrose | 1% (w/v) |
| PVP (polyvinyl pyrrolidone) | 0.5% (w/v) |
| Ascorbic acid | 100 mg/L |
| Citric acid | 150 mg/L |

Adjusted to pH 5.8
Here, the salt is added in an amount corresponding to ¼ of the total amount.

Then, in order to prevent browning the root was placed in a sterilized petri dish containing CS solution (cutting solution, Table 2) supplemented with an antioxidant. The exterior bark of the root was peeled thinly, the resulting root was divided into halves, and sliced off into pieces sized length×width×thickness=~0.5~0.7 cm×0.5~0.7 μm×0.2~0.5 mm such that the pieces contained the actively dividing cambium. FIG. 1(*a*)-B shows an explant which was sliced off into above size to contain the cambium of a main root of wild ginseng.

1-2: Treatment of Osmotic Agent on Explants Containing Cambium of Wild Ginseng Main Root Each of explant prepared in Example 1-1 was treated with osmotic stress in order to induce necrosis of differentiated tissues, i.e., xylem, phloem, pith, etc., and only to allow a meristem, the cambium, to survive. The explant was blotted to a pre-culture medium (medium 1, Table 3) covered with a filter paper, placed into a flask containing 1M sucrose (Duchefa, Netherland) solution, and stored under a refrigeration condition for 16~24 hr to apply an osmotic stress. The explant was then treated with 0.05M sucrose solution for 5 min and again with 0.1M sucrose solution for 5 min to remove the stress by high concentration of sucrose. Then, the explant was placed into a pre-culture medium (medium 1) covered with a filter paper to remove moisture.

TABLE 2

| CS (cutting solution) | |
|---|---|
| Ingredients | Concentration |
| PVP (Polyvinyl pyrrolidone) | 0.5% (w/v) |
| Ascorbic acid | 100 mg/L |
| Citric acid | 150 mg/L |

TABLE 3

Composition of pre-culture medium (medium 1)

| | Composition | mM | mg/L |
|---|---|---|---|
| Macroelements | $Ca(NO_3)_2$ | 2.35 | 471.26 |
| | $NH_4NO_3$ | 5 | 400 |
| | $MgSO_4 \cdot 7H_2O$ | 1.5 | 180.54 |
| | $K_2SO_4$ | 5.68 | 990 |
| | $CaCl_2 \cdot 2H_2O$ | 0.65 | 72.5 |
| | $KH_2PO_4$ | 1.25 | 170 |

| | Composition | μM | mg/L |
|---|---|---|---|
| Microelements | $MnSO_4 \cdot 4H_2O$ | 131.94 | 22.3 |
| | $ZnSO_4 \cdot 7H_2O$ | 29.91 | 8.6 |
| | $Na_2MoO_4 \cdot 2H_2O$ | 1.03 | 0.25 |
| | $H_3BO_3$ | 100.27 | 6.2 |
| | $CuSO_4 \cdot 5H_2O$ | 1.0 | 0.25 |
| | FeNa-EDTA | 100 | 36.7 |
| Vitamin | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 2.96 | 1.0 |

1-3: Induction of Homogenous Cell Line from an Explant Containing Cambium of Wild Ginseng In order to induce a cambium-derived homogenous cell line having a division potential, the explant treated with osmotic stress in Example 1-2 was plated in a medium for cell line induction (medium 2, Table 4). The medium used in the plating to is shown in Table 4. The transferred explant was cultured under a dark condition of 22±1° C.

TABLE 4

Composition of a medium for inducing cambium-derived
homogenous cell line induction (medium 2)

| Composition and condition | Concentration used and condition |
|---|---|
| Salt | Full strength WPM |
| Sucrose | 3% (w/v) |
| IAA (indole-3-acetic acid) | 2 mg/L |
| pH | 5.8 |
| Gelrite | 0.3% (w/v) |
| Ascorbic acid | 100 mg/L |
| Citric acid | 150 mg/L |

At this time, the explant which did not undergo osmotic stress and laid onto the cell line induction medium fast showed a yellow color around cambium in the early stage within 2~3 days and the color spread out into whole explant depending on time, as stated in <Table 5>. For the purpose of continuously inducing a homogenous cell line and continuously proliferating it, the explant showing yellow response around cambium was sub-cultured in an optimum medium for isolating and proliferating a cambium-derived homogenous cell line which has a division potential (medium 3), but browning was intensified and no response other than browning response appeared over time.

In contrast, it was observed that the explant plated onto the medium for homogenous cell line after the induction and removal of the osmotic stress showed no induction of homogenous cells from tissues other than cambium, as stated in <Table 5>. That is, in case of the explant plated after the osmotic treatment and removal, the cambium of the explant began to turn into light yellow in 3~7 culture days. About 7~14 days thereafter, it was also observed that a round cell line was induced in the region of light yellow. FIG. 1(a)-C shows the appearance of the homogenous cell line having cambium-specific division potential among cambium-containing explants of wild ginseng.

Meanwhile, when the explant with osmotic treatment was cultured in a conventional medium containing 2,4-D, which is typically used in the culture of Panax ginseng, e.g., ginseng, wild ginseng, etc., not in the medium for homogenous cell line induction, it was observed that whole explant began to turn into yellow in 7~10 days and a cell line was induced from the surface of the whole explant about 7~14 days thereafter.

TABLE 5

Comparison of responses between explants with or without osmotic treatment

| Treatment type | Untreated | 16 hr-treated | 20 hr-treated | 24 hr-treated |
|---|---|---|---|---|
| Aspect | At the initial stage after the inoculation, a yellow reaction progressed and had the tendency to spread throughout the entire explant. Then, a severe browning color reaction progressed throughout the explants including the cambium, and the induction of a homogeneous cell line, specific in the cambium, was no longer shown | Induction of cells was observed specifically in cambium. As a result of treatment of osmotic stress for varying time, similar results were observed. That is, there was no significant difference depending on time. | | |

1-4: Proliferation of Isolated Homogenous Cell Line Derived from Wild Ginseng Cambium The homogenous cell line induced in Example 1-3, which has a division potential derived from cambium, were used for proliferation. The medium shown in <Table 7> based on salt composition as set forth in <Table 6> was used as an optimum medium for homogenous cell line proliferation.

TABLE 6

Basic salt composition of optimum medium for isolating and
proliferating homogenous cell line derived from cambium

| | Composition | mM | mg/L |
|---|---|---|---|
| Macroelements | $CaCl_2 \cdot 2H_2O$ | 2.99 | 332.02 |
| | $KH_2PO_4$ | 1.25 | 170 |
| | $KNO_3$ | 18.79 | 1900 |
| | $MgSO_4$ | 1.5 | 180.54 |
| | $NH_4NO_3$ | 20.61 | 1650 |

| | Composition | uM | mg/L |
|---|---|---|---|
| Microelements | $CoCl_2 \cdot 6H_2O$ | 0.11 | 0.025 |
| | $CuSO_4 \cdot 5H_2O$ | 0.1 | 0.025 |
| | FeNa-EDTA | 100 | 36.7 |
| | $H_3BO_3$ | 100.27 | 6.2 |
| | KI | 5.0 | 0.83 |
| | $MnSO_4 \cdot 4H_2O$ | 100 | 16.9 |
| | $Na_2MoO_4 \cdot 2H_2O$ | 1.03 | 0.25 |
| | $ZnSO_4 \cdot 7H_2O$ | 29.91 | 8.6 |
| Vitamins | Glycine | 26.64 | 2.0 |
| | myo-Inositol | 554.94 | 100 |
| | Nicotinic acid | 4.06 | 0.5 |
| | Pyridoxine-HCl | 2.43 | 0.5 |
| | Thiamine-HCl | 0.3 | 0.1 |

TABLE 7

Composition of optimum medium for isolating and proliferating
homogenous cell line derived from cambium (medium 3)

| Composition and condition | Concentration used and condition |
|---|---|
| Salt | Full strength MS |
| Sucrose | 3% (w/v) |
| 2,4-D (2,4-dichlorophenoxyacetic acid) | 2 mg/L |
| pH | 5.8 |
| Gelrite | 0.3% (w/v) |
| Ascorbic acid | 100 mg/L |
| Citric acid | 150 mg/L |

As shown in FIG. 1(a)-C, the sub-culture in medium 3 as set forth in <Table 7>, after induction of cambium-specific homogenous cell line using osmotic stress treatment and medium 2, made it possible to isolate homogenous cell line having a division potential derived from cambium after 10~20 days culture. The homogenous cell line derived from the wild ginseng cambium was again cultured in the same medium to proliferate the homogenous cell line having a division potential. FIG. 1(a)-D is the appearance of the homogenous cell line specifically derived from cambium, when proliferated in the medium 3 as set forth in <Table 7>.

1-5: Observation of Characteristics of Isolated Cell Line

The cell line derived from the wild ginseng cambium was placed in a flask filled with a liquid medium of <Table 8> and cultured under a dark condition in a 25±1° C., 100 rpm, rotary shaker. The sub-culture period was fixed into 2 weeks to allow the culture cell to maintain high vitality at logarithmic growth phase. Meanwhile, a callus derived from the ginseng cotyledon was also cultured in medium 4 of <Table 8> and compared with the homogenous cell line derived from the wild ginseng cambium according to the present invention.

TABLE 8

Suspension medium in *Panax ginseng*. (medium 4)

| Composition and condition | Concentration and condition |
|---|---|
| Salt | Full strength MS |
| Sucrose | 3% (w/v) |
| 2,4-D (2,4-dichlorophenoxyacetic acid) | 2 mg/L |
| pH | 5.8 |

First, as a result of observation of the degree of cell aggregation using biological microscope CX31 (Olympus, Japan), the cell line according to the present invention was present as 95% or more of single cell level in suspension culture, and as shown in FIG. 1(b)-A, it was shown to have multiple small vacuoles and to be in an undifferentiated state. However, in case of a callus derived from the ginseng cotyledon (Korea Research Institute of Bioscience and Biotechnology, KCTC PC10224), no multiple and small vacuoles were observed and, instead, one large vacuole was observed, as shown in FIG. 1(b)-B.

TABLE 9

Type of cell aggregates of *Panax ginseng* long-term cultures

| Large cell aggregates | Moderate cell aggregates | Small cell aggregates | Single cell population | Explant source |
|---|---|---|---|---|
| 90% | 7% | 2% | 1% | Cotyledon |
| 0 | 0 | 5% | 95% | Cambium |

Large cell aggregates, size higher than $1.5 \times 10^3$ μm;
Moderate cell aggregates $1 \times 10^3$ μm;
Small cell aggregates $4 \times 10^2$ μm < size < $1 \times 10^3$ μm Meanwhile, in order to examine the possibility of mass culture, a callus derived from the cotyledon of ginseng and homogenous cells derived from the cambium of wild ginseng according to the present invention were each cultured in an airlift bioreactor (Sungwon Cytech, Korea) having the inner volume of 3 L. The liquid medium of <Table 8> was used, and the culture was maintained at 25±1° C. under a dark condition As a result, while the doubling time of the culture derived from the cotyledon of ginseng was 21 days in a flask, it increased to 28 days in the reactor, as shown in <Table 10>. It was considered that the generation of growth ring in a reactor, cell aggregation, and the sensitivity to shear stress due to rigid cell wall would contribute to the decreased cell viability.

Meanwhile, the doubling time was 3~4 days for a culture of cells derived from the cambium of open field true wild ginseng, which was little different or rather shortened between both in a flask and a reactor. The culture of homogenous cells derived from the cambium formed very small area of growth rings in the bioreactor and the rings of inner wall of the bioreactor were conveniently removed when the medium is moved by simple stimuli. Further, as the cell lines have small aggregation, small cell size, multiple vacuoles and low sensitivity to shear stress, thereby do not bring about the decrease in cell viability.

TABLE 10

Doubling times of homogenous cell line derived from wild *ginseng* cambium and cells derived from *ginseng* cotyledon in liquid suspension culture and bioreactor.

| | Doubling time (day) | |
|---|---|---|
| Explant source | flask | Bioreactor |
| Cotyledon | 21 | 28 |
| Cambium (2,4-D treatment) | 5 | 3~4 |

1-6: Treatment of Elicitors

The following experiment was carried out by employing two groups of cell lines cultured in suspension for 14 days, as described in Example 1-5.

Briefly, (1) the cell line cultured in suspension for 14 days (Growth stage: experimental group 1) and (2) a cell line obtained by further culturing said cell line for 14 days in the dark in a medium prepared by adding 3~5 wt % (g/L) of raw sugar and 100 μM of methyl jasmonate to distilled water, were each harvested, and used in the following.

Example 2

Drying of Homogeneous Cell Line Derived from Wild Ginseng Cambium And Preparation of Extract Thereof The cell lines of two treatment groups prepared in Example 1 were dried and extracted as follows:
(1) Preparation of Hot-Air Dried and Pulverized Cell Line
(i) The cell line separated from the culture medium was hot-air dried at about 90° C.
(ii) The dried cell line was pulverized using a pulverizer.
(2) Preparation of Freeze Dried and Pulverized Cell Line
(i) The cell line separated from the culture medium was frozen to the ultra-low temperature state (−70° C.), and then slowly dried under a reduced pressure while being maintained at a room temperature (25° C.) or greater.
(ii) The dried cell line was pulverized using a pulverizer.
(3) Preparation of Extract Using Distilled Water
(i) Each 500 g of the cell lines which were isolated from culture medium, hot-air dried cell lines, and freeze dried cell lines was extracted with 5,000 ml of distilled water while shaking for 6 hour at 50° C.;
(ii) After said dissolution, the extract was centrifuged at 3,000 g for 10 min and the supernatant was collected to obtain a distilled water-soluble product; and
(iii) The distilled water-soluble product was concentrated under a reduced pressure using a rotary vacuum concentrator.
(3) Preparation of Extract Using Ethanol
(i) Each 500 g of the cell lines which were isolated from culture medium, hot-air dried cell lines, and freeze dried cell lines was extracted with 5,000 ml of ethanol while shaking for 6 hour at 50° C.;
(ii) After said dissolution, the extract was centrifuged at 3,000 g for 10 min and the supernatant was collected to obtain an ethanol-soluble product; and
(iii) The ethanol-soluble product was concentrated under a reduced pressure using a rotary vacuum concentrator.

Reference: Experimental Animals and Statistical Analysis

All experimental data in the following Examples were expressed as mean±standard error, by putting together the results obtained in each experiment, using Sigmaplot 5.0 (SPSS Inc., Chicago, Ill.). The data were tested for statistical significance using Student's test, and was considered significant if P value does not exceed 0.05.

6~7 week old C57BL/6 mice and Balb/c mice (Orient Bio Inc., Seongnam-si, Gyeonggi-do, Korea) were used in the experiments while being maintained in a temperature & humidity-controlled cage (Daejong Instrument Industry Co. Ltd., Korea).

Example 3

Cytotoxicity Test

In order to determine the dose range of samples to be used in the experiment, the cytotoxicity was examined as follows.

3-1: Effect of the Administration of Samples on Weight Change

First, the mice of the control and experimental groups were weighed prior to the administration of samples, and the results were compared with those of after administration. The control group was provided with a solid feed only, and experimental groups 1 and 2 were ad libitum fed to a pulverized feed containing 5 wt % of the hot-air dried and pulverized cell line of Example 2. Particularly, the experimental group 1 was administered with a hot-air dried and pulverized material of the cell line cultured in suspension for 14 days in Example 1-6, and the experimental group 2 was administered with a hot-air dried and pulverized material of cell lines obtained by further culturing said cell line of Example 1-6 for 14 days in the dark in a medium prepared by adding 3~5 wt % (g/L) of raw sugar and 100 μM of methyl jasmonate to distilled water. Each group consisted of 10 mice.

The weights of the control group (group A), experimental group 1 (group B), and experimental group 2 (group C) were 20.44±0.76 g, 21.76±0.94 g, and 20.57±0.73 g, respectively, prior to the administration of samples, and the weights of above groups were 22.32±0.82 g, 24.23±0.68 g, and 23.14±0.55 g, respectively, after the administration of samples for 14 days. There were no significant differences between the groups.

3-2: Effect of Consumption of Samples on Cell Numbers of Immune Organs

In order to further confirm the effect of the administration of the samples on immune organs, the control and experimental groups were examined for the cell numbers of immune organs after the administration of the samples. After the administration of the samples, the tissues of murine organs, i.e., spleen and thymus, were isolated. The red blood cells were removed by hypotonic shock, and the cells within the organs were isolated and counted using hemocytometer with a microscope. The condition for administration was as described in Example 3-1.

Figure 3:
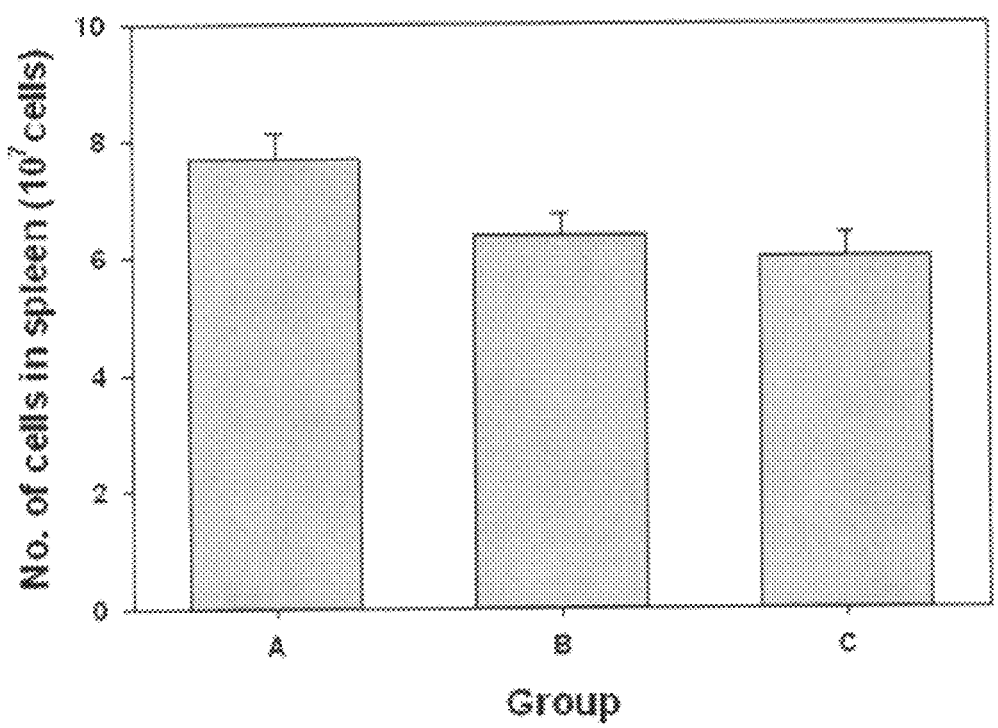
FIG. 3 presents a graph showing the numbers of spleen cells for a control group (A) and experimental groups (B and C) before the administration and at 14 days after the administration of the cell line according to the present invention.

As a result, as shown in FIG. 3, the numbers of the spleen cells were $7.68±0.46×10^7$ for the control group (group A), $6.35±0.40×10^7$ for experimental group 1 (group B), and $5.99±0.40×10^7$ for experimental group 2 (group C), and there were no significant differences between the groups.

Figure 4:
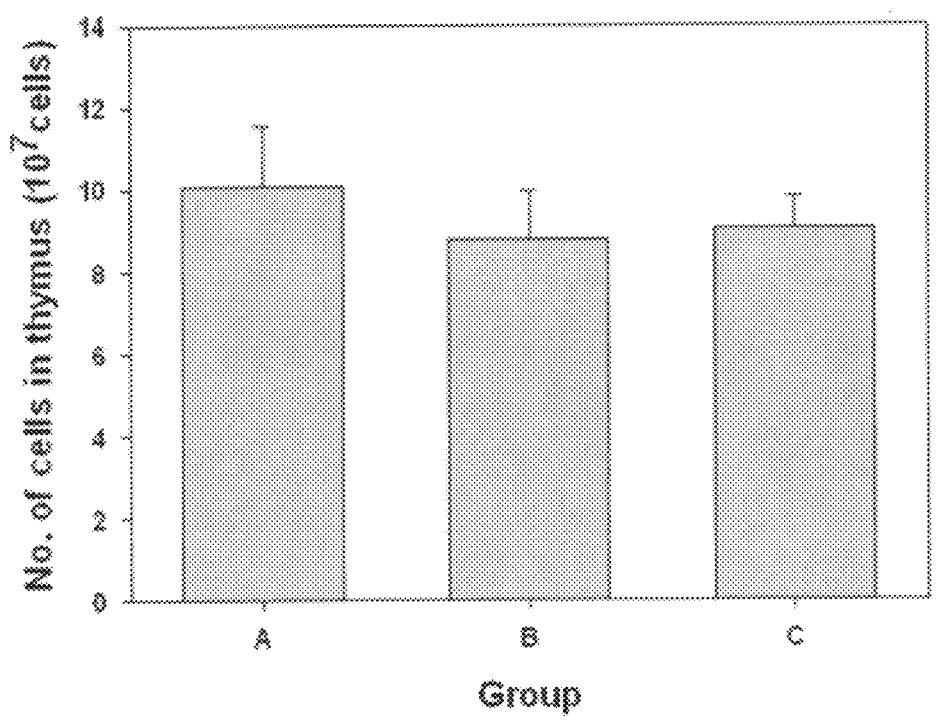
FIG. 4 presents a graph showing the numbers of thymocytes for a control group (A) and experimental groups (B and C) before the administration and at 14 days after the administration of the cell line according to the present invention.

Further, as shown in FIG. 4, the numbers of the thymus cells were $10.10±1.44×10^7$ for the control group (group A), $8.80±1.14×10^7$ for experimental group 1 (group B), and $9.04±0.77×10^7$ for experimental group 2 (group C), and there were no significant differences between the groups.

As shown above, after 14 day-administration of the homogenous cell lines derived from the cambium of wild ginseng according to the present invention, the weight, the cell numbers of the primary (thymus) and the secondary immune organs (spleen) were measured. As a result, the number of immune organs did not significantly decrease, which confirmed no cytotoxicity of the cell lines on immune organs.

Example 4

Measurement of NK Cell Activity According to the Administration of Cell Lines Derived from the Cambium of Wild Ginseng 4-1: Measurement of NK Cell Activity According to the Administration of Cell Lines Derived from the Cambium of Wild Ginseng The control group was administered with a feed only, and experimental groups 1 and 2 were administered with a feed containing a pulverized dried cell line according to the present invention, in the same manner as in Example 3 for 14 days. Then, the spleen cells were isolated, and measured for cytotoxicity at E:T ratio of 40:1 with Yac-1 target cells (E (Effector cell): NK cell; T (Target cell): Yac-1 cell).

Briefly, target cells (YAC-1) were washed once with PBS by using a centrifuge (UNION 32R, Hanil, Seoul, Korea), and suspended in 1 mL of PBS to $1×10^6$ cells/mL. To the cell suspension was added 10 μl, of 3,3'-dioctadecyloxacarbocyanine (DiOC), and the mixture was placed in a 37° C. $CO_2$ incubator for 20 min, and washed two-times with PBS, followed by suspending in 1 mL of complete medium. After adjusting the concentration of effector cells (NK cell) considering E:T ratio of 40:1, the effector cells, target cells, and propidium iodide (PI) were added to a 5 mL test tube, and the tube was centrifuged at 1,000 g for 30 sec. After 4 hour-incubation, the cells were assayed using FACScan; Becton Dickinson (Sunyvale, CD, USA).

Figure 5A:
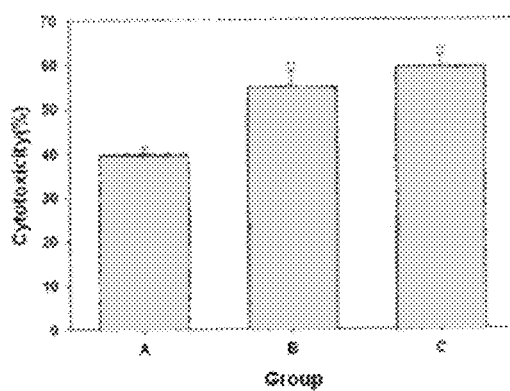
FIG. 5 presents a graph showing the activities of NK cells for a control group (A) and experimental groups (B and C) before the administration and at 14 days after the administration of the cell line according to the present invention.
Figure 5B:
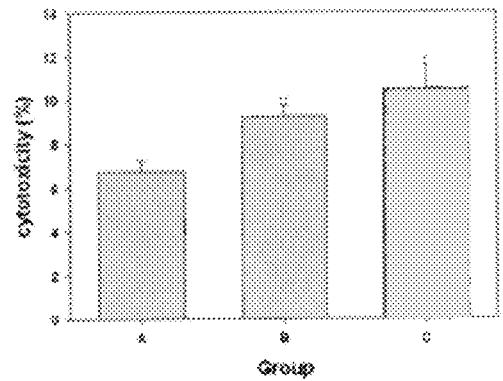

In the first experiment, as shown in FIG. 5A, the results were 39.74±1.70% for the control group (group A), 54.82±3.79% for the experimental group 1 (group B), and 59.12±2.84% for the experimental group 2 (group C), respectively. The values of the experimental groups B and C were significantly increased compared to that of the control group (**, P<0.01). In the second experiment, as shown in FIG. 5B, the results were 6.75±0.48% for the control group (group A), 9.25±0.50% for the experimental group 1 (group B), and 10.44±1.13% for the experimental group 2 (group C). The values of the experimental groups B and C were significantly increased compared to that of the control group (*, P<0.05; **, P<0.01).

Figure 6:
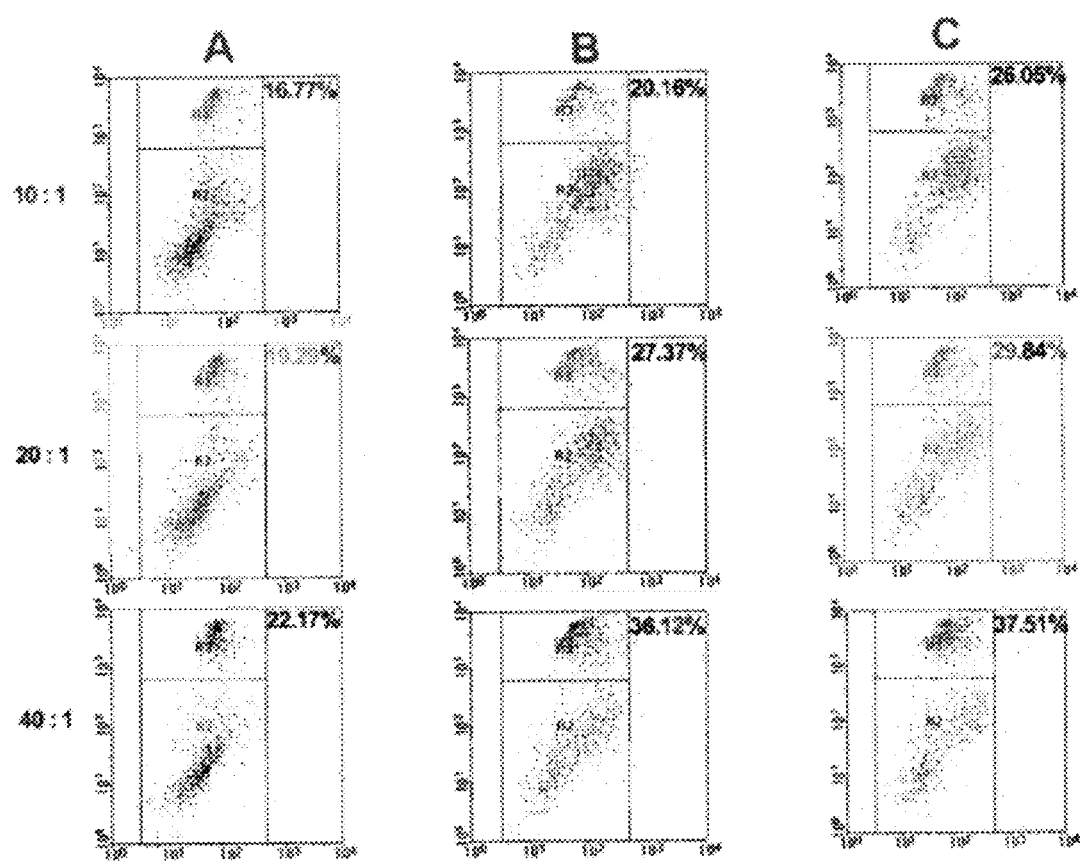
FIG. 6 presents a graph showing the activities of NK cells for a control group (A) and experimental groups (B and C) at E:T ratios of 10:1, 20:1 and 40:1, before the administration and at 14 days after the administration of the cell line according to the present invention.

Moreover, experiments were further carried out at E:T ratios of 10:1, 20:1 and 40:1 in the same manner as above. As shown in FIG. 6, the Yac-1 cell numbers of the experimental groups 1 and 2 were significantly decreased compared to those of the control groups, which confirmed that the activity of NK cells responsible for innate immunity was largely increased in the experiment groups. In particular, the activity was most excellent for the experimental group 2 treated with elicitors.

4-2: Measurement of NK Cell Activities According to the Administration of Cell Lines Derived from the Cambium of Wild Ginseng, a Culture Medium Thereof, and a Control Group of Wild Ginseng As experimental groups, feeds containing each of the pulverized, freeze dried cells of Example 1-6 (A cell) and the culture medium obtained in Example 1-6 (A culture medium) were administered to Balb/c mice, which were previously injected subcutaneously with $5×10^4$ cells of cancer cell line CT-26 (Korean Cell Line Bank), for 26 days in the same manner as in Example 4-1. The control group was administered with a feed only, and a comparative group was administered with a pulverized, freeze dried material of tissue cultured wild ginseng (Modern Bio Inc., KR). Then, the spleen cells were isolated, and measured for cytotoxicity with Yac-1 target cells (E (Effector cell): NK cell; T (Target cell): Yac-1 cell).

Target cells (YAC-1) were adjusted to $2.5 \times 10^6$ cells/mL in a 10% FBS/RPMI medium, 100 μci of $^{51}Cr$ was added thereto. After labeling for 90 min in a 37° C., 5% $CO_2$ incubator, the cells were washed four times with 5% FBS/RPMI and suspended at a concentration of $2.5 \times 10^5$ cells/mL in 10% FBS/RPMI. The labeled target cells were put into a 96 well U bottom plate at 20 μL/well, and the spleen cell suspension was added thereto at 0.2 mL/well so that the E:T ratio became 80:1, 40:1 and 20:1, respectively. The experiment was carried out triplicately. For measurement of spontaneous release (SR), an equal volume of culture medium was added instead of the spleen cell suspension. For measurement of maximum release (MR), 1% triton X-100 solution was added to.

This plate was centrifuged at 100 g for 5 min, kept in a 37, 5% $CO_2$ incubator for 4 hours, and 0.1 mL of supernatant obtained therefrom was measured for released radioactivity. Experimental releases (ER) were measured in each experimental groups, and the cytotoxicity was calculated as follows.

Cytotoxicity (%)=(ER−SR/MR−SR)×100

Figure 7:
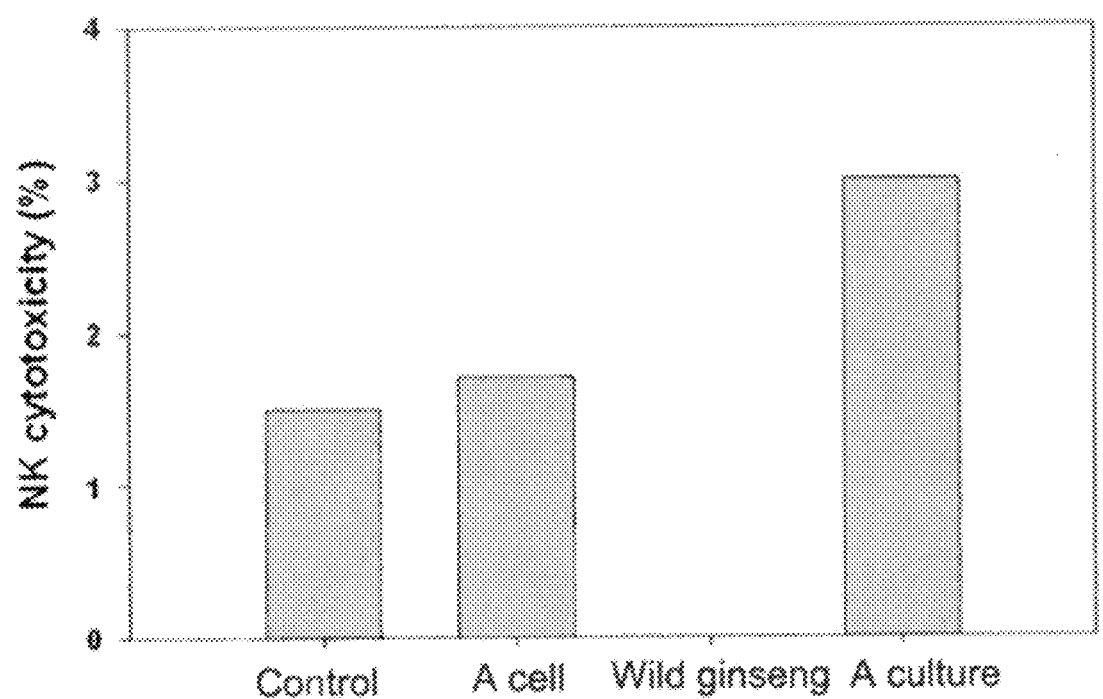
FIG. 7 presents a graph showing the activities of NK cells for a control group (wild ginseng) and experimental groups (the cell line and a culture medium thereof) before the administration and at 26 days after the administration of the cell line according to the present invention.

As shown in FIG. 7, NK cell activities were shown to be increased in the experimental groups using the cell lines derived from the cambium of wild ginseng and the culture medium thereof according to the present invention, compared to the control group (result data obtained at a E:T ratio of 80:1). In contrast, NK cell activity of the wild ginseng comparative group was shown to be lower than that of the control group administered with a feed only. These results indicate that the cell lines and the culture medium according to the present invention have an immune enhancing activity significantly superior to that of ginsengs.

Example 5

Measurement of Antigen-Specific Proliferation Rate of Lymph Node Cells Due to the Cell Line Derived from the Cambium of Wild Ginseng 50 μg of KLH antigen (Keyhole Limpet Hemocyanin: Sigma Chemical, USA) was mixed with an equal amount of CFA (Complete Freund's adjuvant: Sigma Chemical, USA), and the mixture was injected into a subcutaneous base of tail and a sole of a paw in mice. The control and experimental groups were fed ad libitum with a feed and a feed containing the test material, respectively, for 10 days from the next day of the immunization, in the same administration manner as in Example 3.

After 10 days, the cells obtained by extracting lymph nodes from the mice of control group and experimental groups 1 and 2 were added with KLH at a concentration of 0, 0.5, 5 and 50 μg/mL, and were incubated in a 37° C., $CO_2$ incubator. After three days, the cells were added with 10 μg/well of CCK-8 (Dojindo, Japan) and incubated for 4 hours, and O.D value thereof was measured at 450 nm using a spectrophotometer (Peckard spectra conunt TM, A Canberra company).

Figure 8:
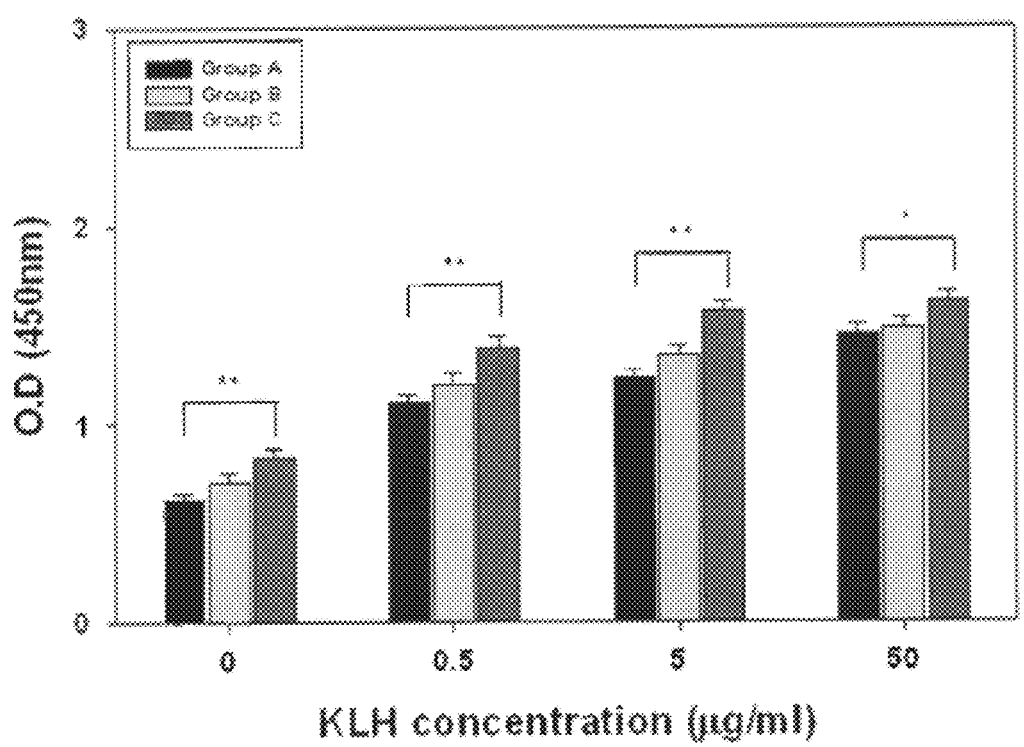
FIG. 8 presents a graph showing effects of antigen stimulation on the lymph node proliferation of a mouse, after the administration of the cell line according to the present invention for 10 days.

As shown in FIG. 8, when no KLH was added (0 μg/mL), the O.D values were 0.61±0.03 for the control group, 0.70±0.05 for the experimental group 1 (group B), and 0.83±0.05 for the experimental group 2 (group C); when 0.5 μg/mL of KLH was added, the O.D values were 1.11±0.04 for the control group, 1.19±0.06 for the experimental group 1 (group B), and 1.38±0.06 for the experimental group 2 (group C); when 5 μg/mL of KLH was added, the O.D values were 1.23±0.04 for the control group, 1.34±0.05 for the experimental group 1 (group B), and 1.56±0.04 for the experimental group 2 (group C); and when 50 μg/mL of KLH was added, the O.D values were 1.45±0.05 for the control group, 1.48±0.04 for the experimental group 1 (group B), and 1.61±0.05 for the experimental group 2 (group C). The O.D value was significantly increased in the experimental group 2 (group C) administered with a pulverized, dried cells, which were derived from the cambium of wild ginseng and cultured with the treatment of elicitors, compared to the control group (*: $P<0/05$, **: $P<0.01$).

The administration of cell line according to the present invention was shown to increase the number of lymph node cells more instantly and rapidly, which indicates that the cell line according to the present invention have an effect to increase the antigen-specific proliferation rate of lymph node cells.

Example 6

Measurement of the Increase in the Number of Bone Marrow Cells by the Administration of the Cell Line Derived from the Cambium of Wild Ginseng 6-1: Measurement of the Number of Bone Marrow Cells According to the Administration of the Cell Line Derived from the Cambium of Wild Ginseng Control group and experimental groups 1 and 2 were fed in the same manner as in Example 3-2, and measured for the number of bone marrow cells. After administration of samples, the marrows of right femoral region were isolated, the red blood cells were removed by hypotonic shock, and the cells within the organs were isolated and counted using hemocytometer with a microscope in a same manner with Example 3.

Figure 9:
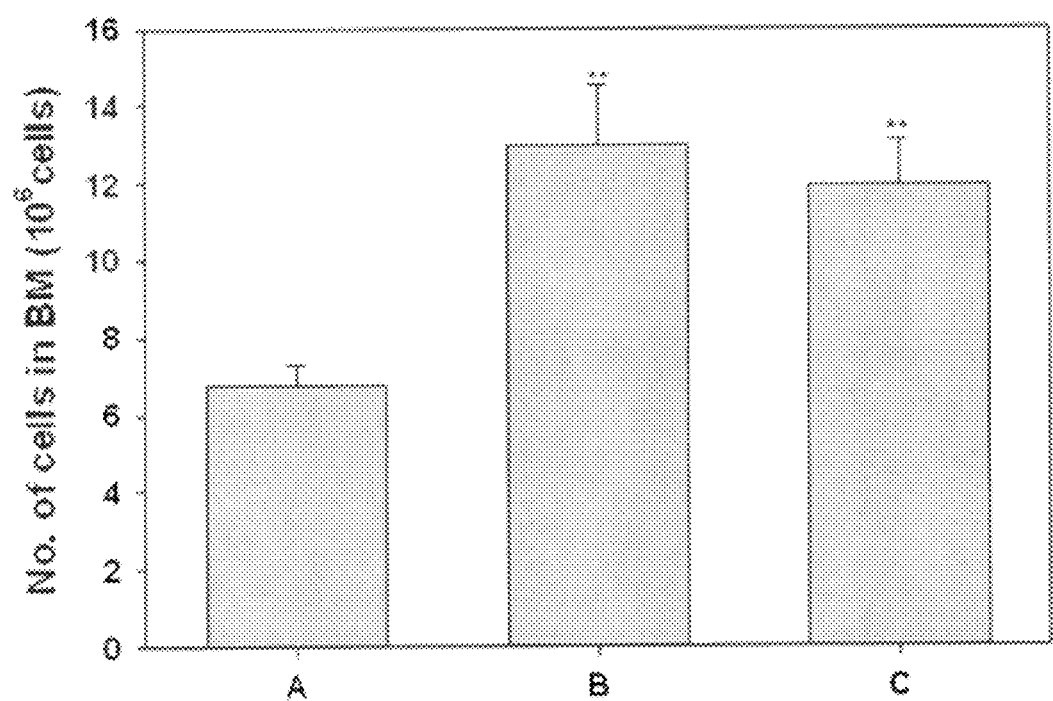
FIG. 9 presents a graph showing the numbers of bone marrow cells for a control group (A) and experimental groups (B and C) before the administration and at 14 days after the administration of the cell line according to the present invention.

As shown in FIG. 9, the numbers of bone marrow cells were $6.75 \pm 0.56 \times 10^6$ for the control group (group A), $12.93 \pm 0.52 \times 10^6$ for the experimental group 1 (group B), and $11.91 \pm 0.39 \times 10^6$ for the experimental group 2 (group C). The cell numbers were significantly increased in the experimental groups 1 and 2, compared to the control group (**, $P<0.01$).

While existing radiotherapy or chemotherapy had a problem of inevitably deteriorating immune function due to side effects such as inhibiting the production of blood cells, the cell line according to the present invention has the effects of increasing the number of bone marrow cells, being useful as an immune-enhancing agent for blocking the deterioration of immune function.

Meanwhile, the increase in the number of bone marrow cells means that the cell line according to the present invention has an activity of strengthening hematopoiesis which provides the preventive and therapeutic effects on anemia.

6-2: Measurement of the Number of Bone Marrow Cells According to, the Administration of the Cell Line Derived from the Cambium of Wild Ginseng, the Culture Medium Thereof, and the Wild Ginseng Control Group As experimental groups, feeds containing each of the pulverized, freeze dried cells of Example 1-6 (A cell) and the culture medium obtained in Example 1-6 (A culture medium) were administered to Balb/c mice which were previously injected subcutaneously with $5 \times 10^4$ cell line of cancer cells CT-26 (Korean Cell Line Bank), for 26 days in the same manner as in Example 3-1. The control group (CTR) was administered with a feed only, and a comparative group was administered with a pulverized, freeze dried material of tissue cultured wild ginseng (Modern Bio Inc., KR). Then, the number of bone marrow cells was measured. After administration of samples, the marrows of right femoral region were isolated, the red blood cells were removed by hypotonic shock, and the cells within the organs were isolated and counted using hemocytometer with a microscope in a same manner with Example 3.

Figure 10:
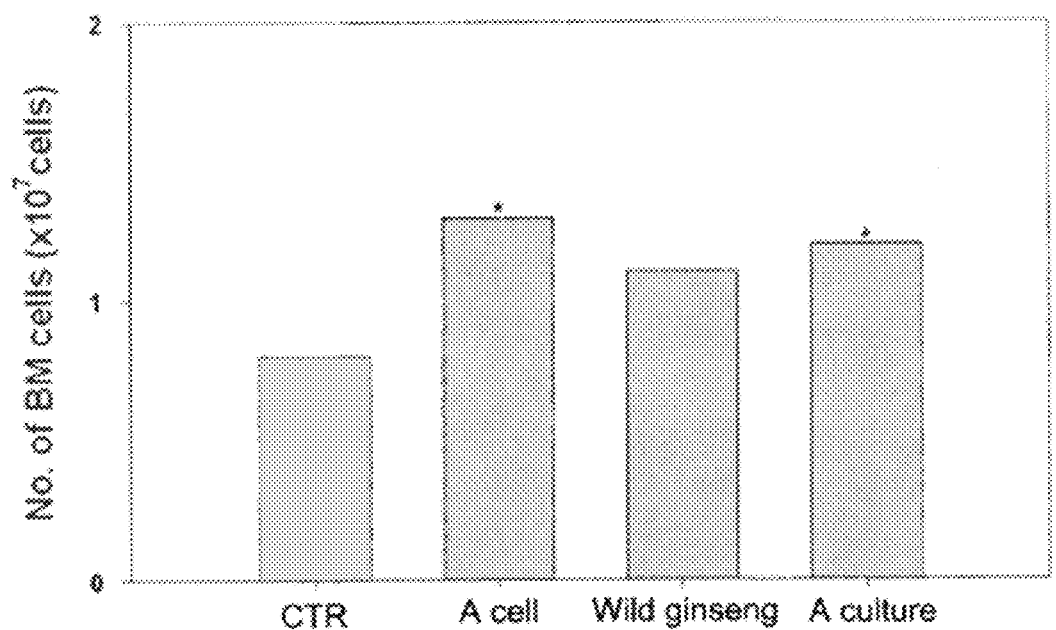
FIG. 10 presents a graph showing the numbers of bone marrow cells for a control group (wild ginseng) and experimental groups (the cell line and a culture medium thereof) at 26 days after the administration of the cell line according to the present invention.

As shown in FIG. 10, when the cell line (A cell) and the culture medium thereof. (A culture medium) according to the present invention were administered, the numbers of bone marrow cells were significantly increased to $1.3 \times 10^7$ cells and $1.2 \times 10^7$ cells, respectively, compared to the control group (*, P<0.05). In contrast, when the wild ginseng comparative group was administered, the number was increased compared to the control group, but the degree of increase was lower than those of the cell line and the culture medium thereof according to the present invention.

Example 7

Measurement of Levels of Hemoglobin, Platelet, Red Blood Cell, and White Blood Cell Patients were administered with a pulverized, hot-air dried cell line of Example 2, by 2 g per day (each 1 g in the morning and evening) or 3 g per day (each 1 g in the morning, noon, and evening). The levels of Hb (hemoglobin), RBC (red blood cell), PLT (platelet), and WBC (white blood cell) were measured before and after the administration. The period of administration and the information on the patients are shown in FIG. 11. Meanwhile, the measurement results obtained by employing a pulverized, freeze dried cell line (Growth stage) of Example 2 are shown in FIG. 12.

When the cell line derived from the cambium of wild ginseng according to the present invention was administered, all of the levels of hemoglobin, platelet, red blood cell, and white blood cell were increased. The increase in the level of white blood cell suggests that the cell line derived from the cambium of wild ginseng according to the present invention has the effects of increasing the immunity, and the increase in the levels of hemoglobin, red blood cell, platelet, etc., suggests that the cell line derived from the cambium of wild ginseng according to the present invention has the function of hematopoiesis, thereby being effective in the prevention and treatment of anemia.

Preparation Example 1

Pharmaceutical Formulation

Formulation Example 1

Preparation of Tablet

The cell line extract (100 mg) prepared in Example 2 was mixed with corn starch (100 mg), lactose (100 mg) and magnesium stearate (2 mg) to prepare a tablet according to a conventional method.

Formulation Example 2

Preparation of Capsule

The pulverized cell line (500 mg) prepared in Example 2 was filled into a soft gelatin capsule to prepare a capsule.

Formulation Example 3

Preparation of Syrup

The cell line (1 g) prepared in Example 1, high fructose corn syrup (10 g), mannitol (5 g), and appropriate amount of purified water were formulated into 100 mL syrup according to a conventional method.

Formulation Example 4

Preparation of Injectable Formulation

The cell line extract (200 mg) prepared in Example 2 was dissolved while heating in saline (200 mg) containing polyoxyethylene hydrogenated castor oil to prepare an injectable formulation containing the cell line extract in a concentration of 0.1%.

Preparation Example 2

Preparation of Functional Foods—Functional Beverages

Preparation Example 1

The cell line (200 mg) prepared in Example 1 was dissolved in water (96 mL); vitamin C (500 mg) as an adjuvant, citric acid (1 g) as a flavor enhancer, oligosaccharide (1 g), and sodium benzoate (0.05 g) as a preservative were added thereto; and purified water was added to make a total volume of 100 mL, thereby preparing a functional beverage.

Preparation Example 2

The pulverized cell line (200 mg) prepared in Example 2 was dissolved in water (96 mL), vitamin C (500 mg) as an adjuvant, citric acid (1 g) as a flavor enhancer, oligosaccharide (1 g), and sodium benzoate (0.05 g) as a preservative were added thereto, and purified water was added to make a total volume of 100 mL, thereby preparing a functional beverage.

INDUSTRIAL AVAILABILITY

As described above, the homogenous cell line, the lysate, the extract, and the culture medium thereof according to the present invention, which are derived from a natural product, minimize adverse side effects of existing immune-enhancing agents and are safe for the human body. Further, they effectively increase the activity of NK cells responsible for innate immunity, as well as increase the proliferation rate of lymph node cells when the cells were re-exposed to an antigen in a specific immune reaction to enhance acquired immunity, and thus are useful as an immune-enhancing agent. The present invention also effectively increase the number of bone marrow cells, thus are useful not only as an adjuvant in an immune reaction, but also in the prevention and treatment of anemia through hematopoiesis.

Although the present invention has been described by way of a detailed description in which various embodiments and aspects of the invention have been described, it will be seen by one skilled in the art that the full scope of this invention is not limited to the examples presented herein. Therefore, the substantial scope of the present invention will be defined by the accompanying claims and equivalents thereof.

What is claimed is:

1. A method for enhancing immunity in a mammal, comprising administering to the mammal one or more of the following: a cell line, a lysate of the cell line, an extract of the cell line, and a culture of the cell line, wherein the cell line is: derived from the cambium of Panax ginseng, is in an innately undifferentiated state, and is not callus.

2. The method of claim 1, wherein the cell line is present as single cell level during a suspension culture.

3. The method of claim 1, wherein the cell line is obtained by using an isolation method comprising the steps of: (a) obtaining a Panax ginseng cambium-containing storage root tissue; (b) culturing the cambium-containing storage root tissue in a medium supplemented with indole-3-acetic acid or indole-3-butyric acid to induce a cell line derived from the cambium, wherein an osmotic stress is applied to the cambium-containing storage root tissue before, during, or after the culture; and (c) collecting the induced, cambium-derived cell line.

4. The method of claim 3, which further comprises culturing the cell line collected in step (c) in a medium supplemented with an elicitor and collecting the cell line.

5. The method of claim 3, wherein step (c) is performed by proliferating the induced cambium-derived cell line in a medium which contains one or more of 2,4-dichlorophenoxyacetic acid, picloram and IBA, and then collecting the cambium-derived cell line.

6. The method of claim 4, wherein the elicitor is raw sugar or methyl jasmonate.

7. The method of claim 1, wherein the extract is obtained by extracting the cell line with a solvent selected from the group consisting of distilled water, alcohol, acetone, dimethyl sulfoxide and a mixture thereof.

8. The method of claim 1, wherein any one among the cell line and the lysate, the extract and the culture thereof has an immune enhancing effect by increasing the activity of NK cells.

9. The method of claim 1, wherein any one among the cell line and the lysate, the extract and the culture thereof has an immune enhancing effect by increasing the number of lymph node cells specific for an antigen.

* * * * *